United States Patent

Dickerhoff et al.

[11] Patent Number: 5,514,169
[45] Date of Patent: May 7, 1996

[54] WARMING BLANKET HAVING MULTIPLE INLETS

[75] Inventors: Scott D. Dickerhoff, Manchester; Thomas F. Kappel, St. Louis; Robert A. Virag, Chesterfield, all of Mo.

[73] Assignee: Mallinckrodt Medical, Inc., St. Louis, Mo.

[21] Appl. No.: 463,384

[22] Filed: Jun. 5, 1995

Related U.S. Application Data

[62] Division of Ser. No. 359,223, Dec. 19, 1994, which is a continuation of Ser. No. 924,269, Aug. 3, 1992, Pat. No. 5,384,924.

[51] Int. Cl.⁶ .......................................................... A61F 7/00
[52] U.S. Cl. .................................................................. 607/107
[58] Field of Search ..................................... 607/107, 104, 607/105; 5/423, 424

[56] References Cited

U.S. PATENT DOCUMENTS

| | | | |
|---|---|---|---|
| 2,093,834 | 9/1937 | Gaugler | 607/107 |
| 2,122,964 | 7/1938 | Sweetland | 607/107 |
| 5,336,250 | 8/1994 | Augustine et al. | 607/107 |
| 5,392,847 | 2/1995 | Stephenson | 607/107 |
| 5,405,371 | 4/1995 | Augustine et al. | 607/107 |
| 5,443,488 | 8/1995 | Namaye et al. | 607/107 |

*Primary Examiner*—Mark S. Graham
*Attorney, Agent, or Firm*—David A. Hey

[57] ABSTRACT

The present invention relates to a blanket for use with forced air convection systems, wherein the blanket includes multiple inlet ports. By providing a blanket with multiple inlets, the user has the choice of positioning the air supply or blower unit and the supply hose on either side of the patient. In addition, in a preferred embodiment, the inlet ports are resealable, thus allowing the user to switch inlets during use.

6 Claims, 1 Drawing Sheet

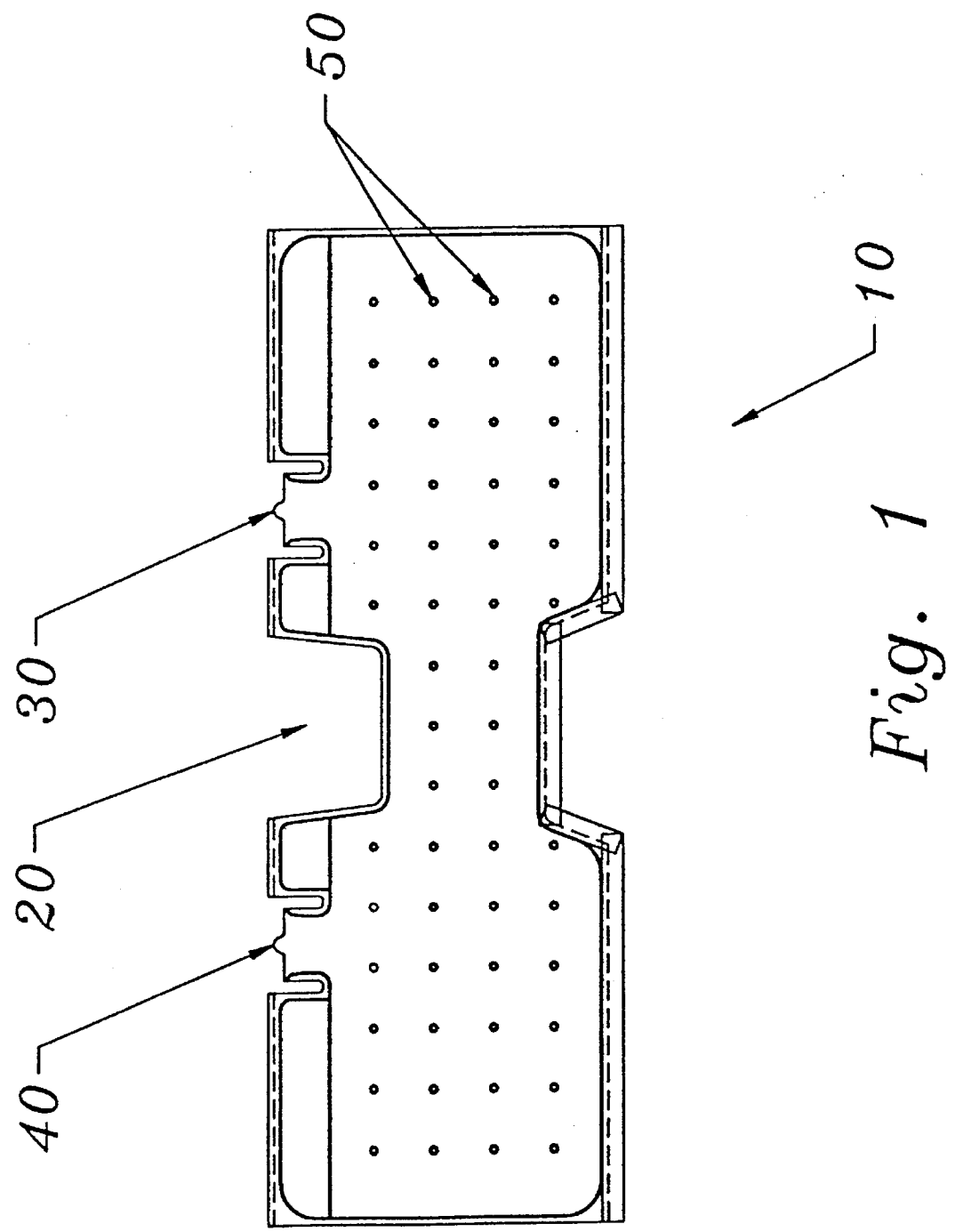

WARMING BLANKET HAVING MULTIPLE INLETS

This is a divisional application under 37 CFR 1.60, of pending prior U.S. application Ser. No. 08/359,223 filed on Dec. 19, 1994, which is a Continuation of Ser. No. 07/924, 269 filed on Aug. 3, 1992 U.S. Pat. No. 5,584,924.

BACKGROUND

Hypothermia is a condition of subnormal body temperature and presents serious consequences to the patient suffering therefrom. It has been shown that nearly seventy five percent of all patients who undergo surgical procedures develop hypothermia. This equates to approximately fourteen million patients a year in the United States alone. The hypothermic condition is brought on by many factors including anesthesia, the air conditioning of the operating room, and the infusion of cold blood, I-V solutions, or irrigating fluids.

Several methods and products have been developed to help prevent hypothermia from occurring; such as the use of infrared lamps, cotton blankets, and warm water mattresses. However, none of these methods and products have proven completely successful. In fact, it has been shown that these methods and products can not even prevent the patients from losing their endogenous heat. (See Journal of Post Anesthesia Nursing, Vol. 5, No. 4, August 1990, pp 254–263).

Another method of helping to prevent hypothermia that has proven very effective is the use of forced warm air convection. As early as 1937, a refrigeration blanket using cold air convection was suggested in U.S. Pat. No. 2,093, 834 to Gaugler. This blanket included a plurality of layers for channeling air flow from an inlet port. Non-inflatable portions were provided around the periphery of the blanket to secure the blanket around the body. Gaugler does not mention hypothermia treatment and does not suggest that the blanket could be used to supply warm air.

U.S. Pat. No. 2,512,559 to Williams also relates to a blanket for providing cooled air to a person. The blanket in Williams comprised a plurality of thin sheets of material connected together at a plurality of discrete locations and connected together in a continuous line about the peripheral edge. An air inlet was provided to communicate with space between the sheets to allow cool air to be supplied thereto. Again, no mention of hypothermia treatment or the supply of warm air is made.

In U.S. Pat. No. 4,572,188 to Augustine et al, a forced air convection system which can supply either cool or warm air to a blanket is described. The blanket in Augustine et al comprises a plurality of inflatable hollow tubes having their interiors connected together through transverse openings. An entry port is provided in the upper surface of the blanket for admitting the cool or warm air and small exit ports are provided through the lower surface to allow the cool or warm air to flow out toward a body covered by the blanket.

Other patents relating to the supply of cool or warm air to a person through an inflatable blanket include U.S. Pat. Nos. 4,660,388 to Greene, Jr.; 4,777,802 to Feher; and 4,867,230 to Voss. Each of these patents describe blankets having various attributes and configurations to supply cool or warm air to the person.

While some of the above systems suggest use in the operating room, they all possess similar disadvantages. In particular, for the system to work, the blanket must be attached to an air supply or blower unit through a hose. The placement of the hose during surgery can be crucial, as full access to the patient can be compromised if the hose must be located in a position which the surgeon wants to occupy. The placement of the hose can create difficulties in locating other equipment such as I–V stands, monitors, etc. necessary for the surgical procedure.

Therefore, there is a need in the art for improvements to forced warm air convection systems.

OBJECTS OF THE INVENTION

It is one object of the present invention to provide a blanket for a forced warm air convection system that allows placement of an air supply hose to be selectively chosen depending on the needs of the surgical procedure to be performed.

It is another object of the present invention to provide a blanket for a forced warm air convection system that allows placement of an air supply hose to be changed during a surgical procedure.

SUMMARY OF THE INVENTION

The above objects and others are accomplished according to the present invention by providing a blanket for a warm air convection system having multiple (at least two) inlets, each such inlet having means whereby such inlet may be selectively closed or opened.

BRIEF DESCRIPTION OF THE DRAWINGS

FIG. 1 is a plan view of a blanket for a forced warm air convection system according to one embodiment of the present invention.

DETAILED DESCRIPTION OF THE INVENTION

FIG. 1 is a plan view of a blanket, generally designated by reference numeral 10, for a forced warm air convection system, wherein the blanket 10, is appropriate for use in the operating room. The blanket 10, shown in FIG. 1 is an upper body blanket, designed to cover the upper body portions of a patient who is undergoing a surgical procedure to lower body portions. The blanket, 10, has a generally rectangular shape and include a head recess portion 20. The blanket 10, comprises two sheets of material which are sealed together along their peripheral edges and are connected together at connection spot welds 50, discretely located on the interior surface portions of the sheets. By connecting the sheets of the blanket 10, in this manner, the blanket 10, may be inflated by supplying air to the interior area formed between the sheets of material.

The blanket 10, further includes a first inlet port 30, and a second inlet port 40. Inlet ports 30, 40 are in communication with the interior of the blanket 10, and may be used to supply air to the interior of the blanket 10, so as to inflate blanket 10. The lower surface (not shown) of the blanket 10, is provided with a plurality of small exit ports to allow warm air to escape from the blanket 10, toward a patient.

In use, the blanket 10, is placed over the upper body of a patient so that the patient's head remains exposed within the head recess portion 20, and the inlet ports 30, 40, are oriented in a direction pointing toward the top of the head of the patient. In this position, one inlet port will be located on each side of the patient's head.

The inlet ports 30, 40, may initially be closed by any suitable means such as sealing, folding, taping, snapping, etc. In the case where the inlet has been permanently sealed, means such as a perforated tear strip may be provided to enable easy opening of the inlet port selected for use. However, such sealing of the inlet ports requires the user to select the inlet port to be used prior to operation of the blanket 10, and does not allow switching to the other inlet port during use. This is because once the permanent seal for such an inlet port has been broken or opened, it is not possible to re-close the inlet port.

Therefore, in a preferred embodiment, the inlet ports 30, 40 will be initially closed by means that allow re-closing. In particular, means such as an adhesive strip, double-sided tape, snaps, zippers, folding flaps, or a ziplock type seal, etc. may be utilized. In a most preferred embodiment, the inlet ports 30, 40 are initially sealed by velcro strips to allow easy opening and re-closing.

The blanket according to the present invention has several advantages. In particular, by providing a blanket with dual inlets, the user has the choice of positioning the air supply or blower unit and the supply hose on either side of the patient. In addition, by providing resealable inlet ports, the user may switch inlets during use. This is particularly advantageous in allowing the surgeon full access to the patient.

The provision of spot welds 50, to connect the separate sheets of the blanket 10, also is advantageous. In particular, the spot welds 50, allow the free flow of warm air in all directions and therefore allow for better heat distribution within the blanket. This can be critical in reducing the occurrence of hot or cold spots within the blanket during use.

The blanket may be formed of any suitable material capable of being sealed together at selected positions and having sufficient strength to allow inflation and adequate air distribution within the inflated portion. Such materials include plastics, non-woven wood pulp compositions, laminated plastic and wood pulp materials, and combinations thereof.

It should be noted that the present invention is primarily concerned with a blanket which can be used to supply warm air to a patient in the operating room during a surgical procedure, so as to help prevent the occurrence of hypothermia. However, it will be evident to one skilled in the art that the blankets according to the present invention could be used in areas other than the operating room, such as in the recovery room, or in the patient's regular hospital room. Further, it will be evident to one skilled in the art that a source of pressurized cooled air could be provided to the blanket according to the present invention to control body temperature of the patient under conditions of hyperthermia.

In addition, while the present invention has been particularly described by reference to a blanket having two inlets, it will be evident to one skilled in the art that any number of inlets could be provided to enable even greater flexibility of use. The placement of additional inlets is limited only by the need to maintain good air distribution and flow within the blanket.

It is also noted that it would be possible to connect a supply source of warm air to each of the inlets when using the blanket according to the present invention. Alternatively a single supply source could be connected to each inlet using a multiply branched supply hose. For example, if there are two inlets, the supply hose could have a y-shaped configuration. Each of these embodiments of using the present invention, may be advantageous in providing more even heat distribution to all parts of the blanket.

The foregoing has been a description of certain preferred embodiments of the present invention, but is not intended to limit the invention in any way. Rather, many modifications, variations and changes in details may be made within the scope of the present invention.

What is claimed is:

1. A method of warming a patient's body, comprising the steps of:
   (a) providing an inflatable blanket for a patient's body, said inflatable blanket having a head end portion for positioning toward a patient's head, said blanket having at least two inlet ports being positioned about said head end portion of said blanket so that, in use, one said inlet port is positioned on one side of a patient's head and another of said inlet ports is positioned on another side of said patient's head, said blanket permitting warm air to escape from said blanket toward the patient's body;
   (b) positioning said blanket with respect to said patient's body so as to permit warm air to escape from said blanket toward the patient's body and thereby warm the patient's body, wherein the head end portion of said blanket is positioned toward the patient's head and one said inlet is positioned on one side of the patient's head and another of said inlet ports is positioned on another side of said patient's head; and
   (c) introducing warm air into at least one of said inlet ports so as to inflate said blanket with warm air and force said warm air through said blanket toward the patient's body, thereby warming the patient's body.

2. The method of claim 1, wherein said head end portion is a head recess portion of said blanket, and wherein said head recess portion is positioned adjacent said patient's head.

3. The method of claim 1, wherein said blanket is adapted for covering at least a portion of said patient's body, and wherein, in step (b), at least a portion of said patient's body is covered by said blanket.

4. The method of claim 1, wherein each of said inlet ports is initially sealed closed, said inlet ports being selectively openable, and wherein prior to step (c), one of said inlet ports is opened.

5. The method of claim 1, wherein said inlet ports are initially sealed closed and are reversibly openable, and wherein prior to step (c), one of said inlet ports is opened.

6. A method of warming a patient's body, comprising the steps of:
   (a) providing an inflatable blanket for a patient's body, said inflatable blanket having a head end portion for positioning toward a patient's head, said blanket having at least two selectively openable inlet ports for inflating said blanket with warm air, said inlet ports being positioned about said head end portion of said blanket so that, in use, one said inlet port is positioned on one side of a patient's head and another of said inlet ports is positioned on another side of said patient's head, said blanket permitting warm air to escape from said blanket toward the patient's body;
   (b) positioning said blanket with respect to said patient's body so as to permit warm air to escape from said blanket toward the patient's body and thereby warm the patient's body, wherein the head end portion of said blanket is positioned toward the patient's head and one said inlet is positioned on one side of the patient's head and another of said inlet ports is positioned on another side of said patient's head;

(c) introducing warm air into one of said inlet ports so as to inflate said blanket with warm air and force said warm air through said blanket toward the patient's body, thereby warming the patient's body, the inlet port used being on the opposite side of the patient from the position of medical personnel heating the patient, and (d) allowing the other inlet port to remain closed.

* * * * *